US006652493B1

(12) United States Patent
Das

(10) Patent No.: US 6,652,493 B1
(45) Date of Patent: Nov. 25, 2003

(54) INFUSION PUMP SYRINGE

(75) Inventor: Kusal K. Das, Wrightstown, PA (US)

(73) Assignee: Animas Corporation, Frazer, PA (US)

( * ) Notice: Subject to any disclaimer, the term of this patent is extended or adjusted under 35 U.S.C. 154(b) by 0 days.

(21) Appl. No.: 09/610,622

(22) Filed: Jul. 5, 2000

(51) Int. Cl.[7] ................................................ A61M 5/00
(52) U.S. Cl. ....................... 604/181; 604/199; 604/218; 604/220; 604/241
(58) Field of Search .................................. 604/181, 154, 604/151, 155, 187, 199, 218, 220, 224, 240, 241

(56) References Cited

U.S. PATENT DOCUMENTS

| | | |
|---|---|---|
| 3,598,120 A | 8/1971 | Mass |
| 3,771,694 A | 11/1973 | Kaminski |
| 3,985,133 A | 10/1976 | Jenkins et al. |
| 4,267,846 A | 5/1981 | Kontos |
| 4,529,401 A | 7/1985 | Leslie et al. |
| 4,543,093 A | 9/1985 | Christinger |
| 4,544,369 A | 10/1985 | Skakoon et al. |
| 4,562,844 A | 1/1986 | Carpenter et al. |
| 4,685,903 A | 8/1987 | Cable et al. |
| 4,710,170 A * | 12/1987 | Haber et al. ................ 604/110 |
| 4,919,650 A | 4/1990 | Feingold et al. |
| 4,978,335 A | 12/1990 | Arthur, III |
| 5,090,962 A | 2/1992 | Landry, Jr. et al. |
| 5,120,314 A | 6/1992 | Greenwood |
| 5,176,502 A | 1/1993 | Sanderson et al. |
| 5,215,536 A | 6/1993 | Lampropoulos et al. |
| 5,259,840 A | 11/1993 | Boris |
| 5,318,537 A | 6/1994 | Van Der Merwe |
| 5,411,488 A | 5/1995 | Pagay et al. |
| 5,485,853 A | 1/1996 | Stubbs |
| 5,505,709 A | 4/1996 | Funderburk et al. |
| 5,522,803 A | 6/1996 | Teissen-Simony |
| 5,647,853 A | 7/1997 | Feldmann et al. |
| 5,658,261 A * | 8/1997 | Neer et al. ............. 128/DIG. 1 |
| 5,681,285 A | 10/1997 | Ford et al. |
| 5,722,956 A * | 3/1998 | Sims et al. ........... 128/DIG. 12 |
| 5,735,825 A | 4/1998 | Stevens et al. |
| 5,741,227 A | 4/1998 | Sealfon |
| 5,779,675 A * | 7/1998 | Reilly et al. ........... 128/DIG. 1 |
| 5,954,697 A | 9/1999 | Srisathapat et al. |
| 6,048,334 A * | 4/2000 | Hirschman et al. ......... 604/154 |
| 6,210,133 B1 * | 4/2001 | Aboul-Hosn et al. .... 417/423.1 |
| RE37,487 E * | 12/2001 | Reilly et al. .......... 128/DIG. 1 |

* cited by examiner

Primary Examiner—Brian L. Casler
Assistant Examiner—Jeremy Thissell
(74) Attorney, Agent, or Firm—Finnegan, Henderson, Farabow, Garrett & Dunner, L.L.P.

(57) ABSTRACT

A syringe for use with an infusion pump, the infusion pump having a cavity for receiving the syringe. The syringe includes a syringe body, a plunger and an end cap. The syringe body has a tube that is open at a first end and transitions to a passage at a second end and a connector extending from the passage, the connector for attachment to an infusion set or tubing. The plunger is slidably mounted inside the tube and comprises a plunger tip and a plunger rod. The plunger tip has a front face that is complementarily received by the second end of the tube and a rear face, the plunger tip forming an interference fit with the tube. The plunger rod has a first end attached to the plunger tip and a second end extending outside the first end of the tube. The plunger rod has a cross-sectional shape that is complementarily received by the cavity of the infusion pump when inserted in only one direction. The end cap is attached to the first end of the tube and has an opening that is shaped to complementarily receive the plunger rod.

19 Claims, 5 Drawing Sheets

INFUSION PUMP SYRINGE

BACKGROUND OF THE INVENTION

The present invention relates to a syringe for an infusion pump. More particularly, the present invention relates to a syringe that fits inside a small infusion pump, such as infusion pumps used by diabetics to inject insulin or other medication at controlled rates.

The present invention is capable of use with the infusion pump having a sealed drive mechanism and improved method of occlusion detection for determining the presence of obstructions in the infusion path set forth in co-pending application Ser. No. 09/335,999, which is incorporated herein by reference.

BRIEF SUMMARY OF THE INVENTION

Briefly stated, the present invention is a syringe for use with an infusion pump. The infusion pump has a cavity for receiving the syringe. The syringe comprises a syringe body, a plunger and an end cap. The syringe body comprises a tube that is open at a first end and transitions to a passage at a second end and a connector extending from the passage, the connector for attachment to an infusion set or tubing. The plunger is slidably mounted inside the tube and comprises a plunger tip and a plunger rod. The plunger tip has a front face that is complementarily received by the second end of the tube and a rear face, the plunger tip forming an interference fit with the tube. The plunger rod has a first end attached to the plunger tip and a second end extending outside the first end of the tube. The plunger rod has a cross-sectional shape that is complementarily received by the cavity of the infusion pump when inserted in only one direction. The end cap is attached to the first end of the tube and has an opening that is shaped to complementarily receive the plunger rod.

In another aspect, the present invention is a syringe for use with an infusion pump. The infusion pump has a cavity for receiving the syringe. The syringe comprises a syringe body, various transitions, a plunger and an end cap. The syringe body comprises a tube that is open at a first end and transitions to a passage at a second end and a connector extending from the passage, the connector for attachment to an infusion set or tubing. The transition from the tube to the second end of the tube comprises rounded corners. The transition from the second end of the tube to the passage also comprises rounded corners. The plunger is slidably mounted inside the tube and comprises a plunger tip and a plunger rod. The plunger tip has a front face that is complementarily received by the second end of the tube and a rear face, the plunger tip forming an interference fit with the tube. The plunger rod has a first end attached to the plunger tip and a second end extending outside the first end of the tube. The plunger rod has a cross-sectional shape that is complementarily received by the cavity of the infusion pump when inserted in only one direction. The end cap is attached to the first end of the tube and has an opening that is shaped to complementarily receive the plunger rod.

BRIEF DESCRIPTION OF THE SEVERAL VIEWS OF THE DRAWINGS

The foregoing summary, as well as the following detailed description of the preferred embodiment of the present invention will be better understood when read in conjunction with the appended drawings. For the purpose of illustrating the invention, there is shown in the drawings an embodiment that is presently preferred. It should be understood, however, that the invention is not limited to the precise arrangements and instrumentalities shown. In the drawings, like numerals are used to indicate like elements throughout. In the drawings.

DETAILED DESCRIPTION OF THE INVENTION

Figure 1:
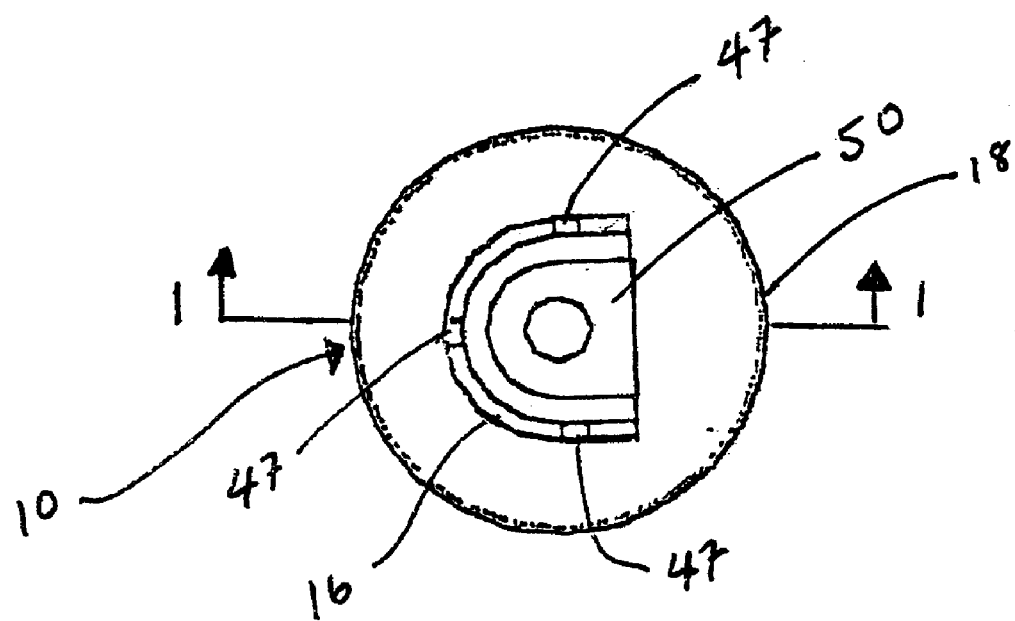
FIG. 1 is a bottom plan view of a syringe according to the present invention.

Certain terminology is used in the following description for convenience only, and is not limiting. The words "right," "left," "lower" and "upper designate directions in the drawings to which reference is made. The words "inward" and "outward" refer to directions toward and away from, respectively, the geometric center of the syringe and designated parts thereof. The terminology includes the words above specifically mentioned, derivatives thereof and words of similar import.

Figure 2:
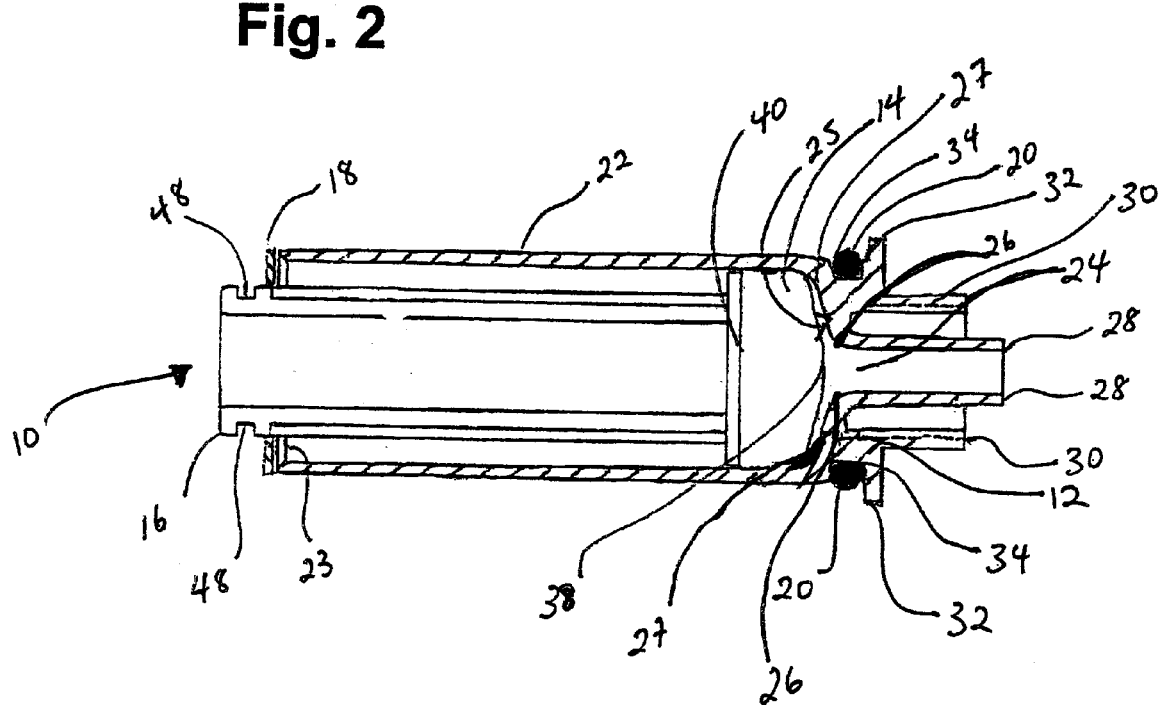
FIG. 2 is a cross-section of the syringe shown in FIG. 1 taken along the line 1—1 of FIG. 1.
Figure 3:
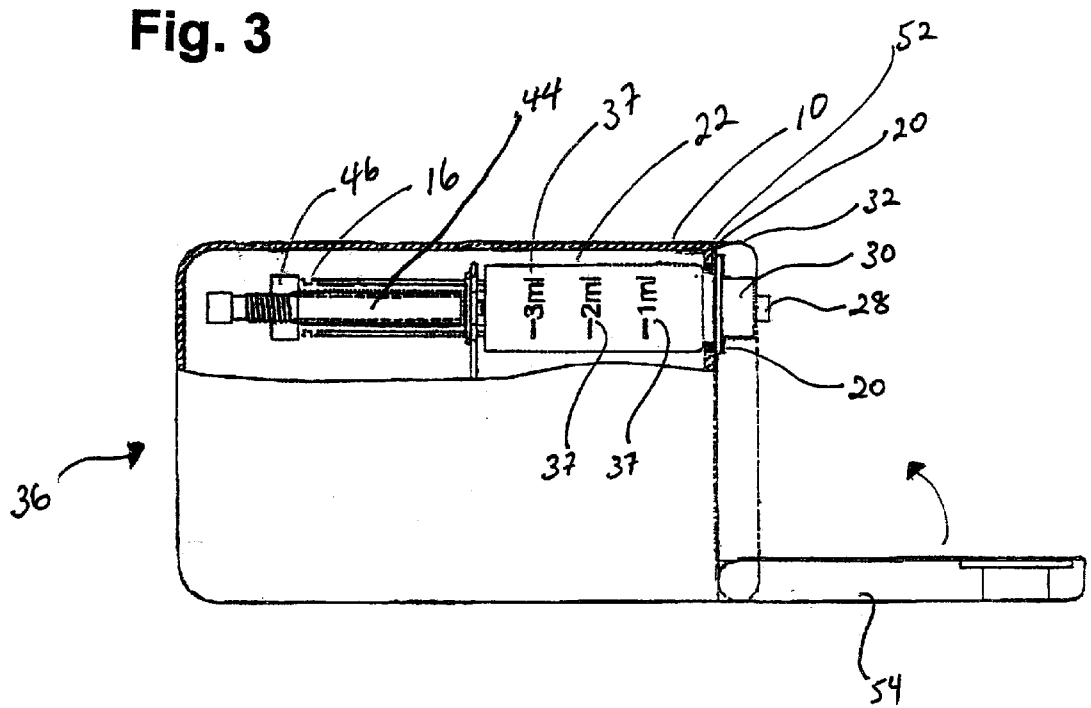
FIG. 3 is a front elevational view, partially in cross-section, of a syringe according to the present invention shown as inserted into an infusion pump.

As shown in FIGS. 1–3, the syringe 10 of the present invention includes a syringe body 12, a plunger tip 14, a plunger rod 16, an end cap 18 and a sealing ring 20. The syringe body 12, which is preferably made from a plastic material such as polypropylene, includes a barrel 22 that preferably comprises a generally cylindrical tube that is open at a first end 23 and transitions to a generally cylindrical passage 24 at a second end 25. The second end of the barrel 25 is generally conical in shape, which facilitates the escape of any air bubbles through the passage 24 when the syringe 10 is to be filled with medication. Moreover, the transition from the tube 24 of the barrel 22 to the second end of the barrel 22 comprises rounded corners 27 to facilitate the escape of air bubbles. Additionally, to further facilitate the escape of air bubbles, the transition 25 between the second end of the barrel and the passage 24 consists of rounded corners 26.

The passage 24 extends into connector 28, which can be connected to an infusion set or tubing (not shown) for delivering the medication contained in the syringe 10 to a desired site. The connector 28 is preferably a Luer connector. The connector 28 also includes locking mechanism 30, preferably an integral Luer-lock, which allows the syringe 10 to be secured to the infusion set or tubing. It should be understood by those skilled in the art that other connectors and/or locking mechanisms could be used without departing from the spirit and scope of the invention.

A generally circular flange 32 extends around the outer periphery of the syringe body 12 between the barrel 22 and the locking mechanism 30. The diameter of the flange 32 is greater than the diameter of the barrel 22. The flange 32 provides a stop for the syringe 10 as it is inserted into an infusion pump 36 (shown in FIG. 3), allowing the syringe 10 to be precisely positioned within the infusion pump 36 with very little effort by a user. The flange 32, together with the outer surface of the second end of the barrel 22, form a groove 34 that extends around the periphery of the syringe body 12. The sealing ring 20 sits within the groove 24, and the sealing ring 20 forms a watertight seal between the inside and outside of the infusion pump 36 when the syringe 10 is fully inserted into the infusion pump 36 up to the flange 32. Although the flange 32 is preferably generally circular in outline, it should be appreciated by those skilled in the art that the shape of the flange 32 could be varied without departing from the spirit and scope of the invention.

Figure 4:
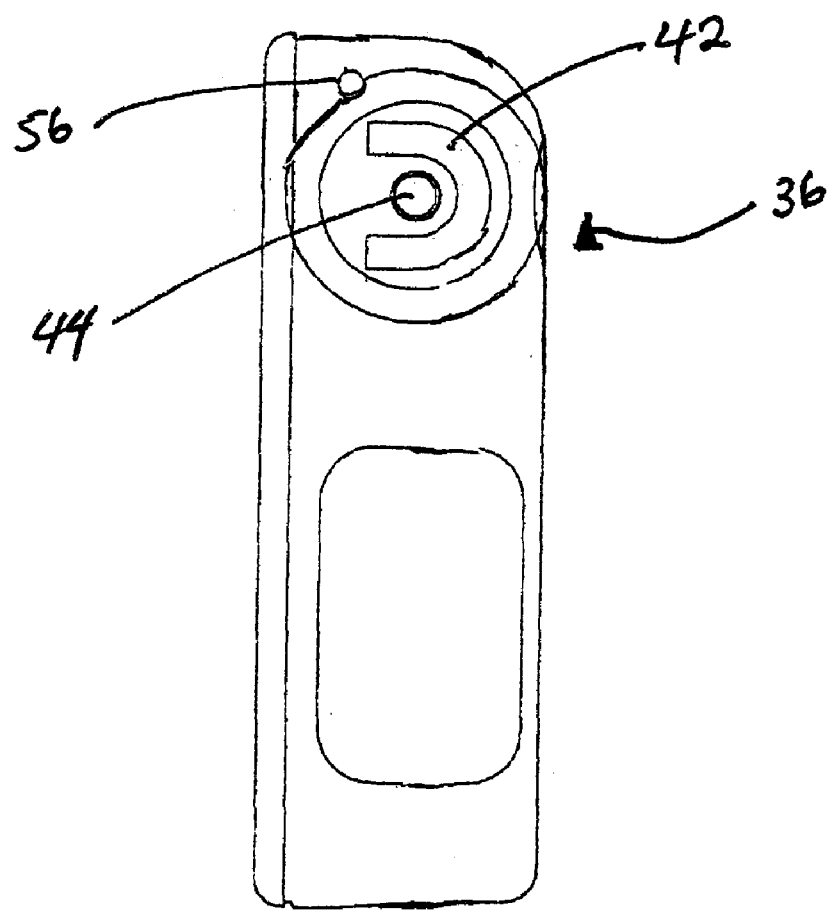
FIG. 4 is a right-side elevational view of an infusion pump with the door removed capable of use with a syringe according to the present invention.
Figure 5:
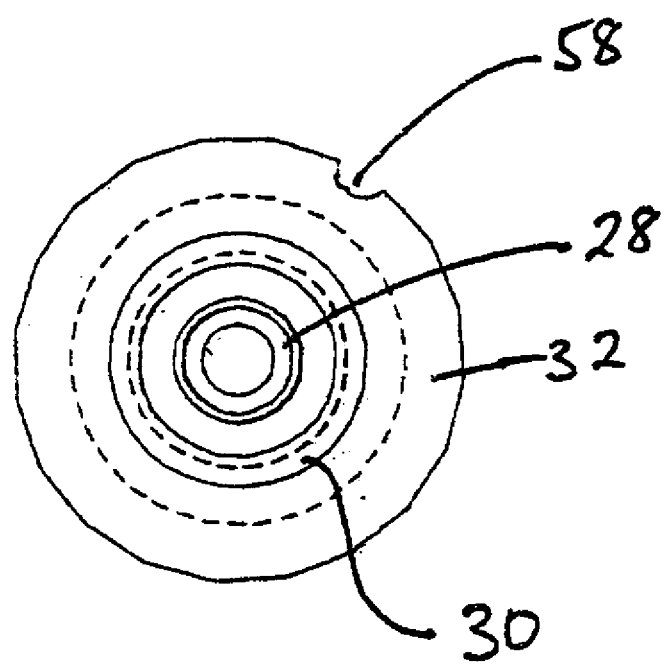
FIG. 5 is a top plan view of a syringe according to the present invention.

As shown in FIG. 5, the flange 32 preferably includes an alignment notch 58, which serves as a guide for inserting the syringe 10 into the infusion pump 36. When the syringe 10 is inserted into the infusion pump 36, the notch 58 in the flange 32 must be aligned with the alignment pin 56 (shown in FIG. 4) of the infusion pump 36. In this way, the alignment notch 58 assists in locating the proper orientation of the syringe 10 for insertion into the infusion pump 36. In addition, the alignment pin 56 and the alignment notch 58 provide a keying mechanism for the syringe 10 that keeps the syringe 10 from rotating after it has been inserted into the infusion pump 36. This is important since it helps prevent the syringe 10 from rotating when an infusion set or tubing is attached by twisting on to the connector 28 and the locking mechanism 30, with adequate torque in order to obtain a good seal and avoid any medication leakage.

As shown in FIG. 3, indications of volume levels 37 can be printed on the outside of the barrel 22 to aid a user in placing the correct amount of medication within the syringe 10 while it is being filled.

The plunger tip 14, which is preferably made from an elastomeric material such as silicone, is preferably generally circular in cross-section, with a shape in cross-section that is identical to the cross-sectional shape of the barrel 22 of the syringe body 12 preferably cylindrical. The plunger tip 14 has a diameter that is just slightly larger than the inner diameter of the barrel 22. When inserted into the barrel 22, an interference fit is created between the plunger tip 14 and the barrel 22, forming a watertight seal between the plunger tip 14 and the barrel 22. The front face 38 of the plunger tip 14 is conical in shape so that it may be complementarily received by the conical second end 25 of the barrel 22. Thus, the plunger tip 14 can be pushed up against the second end of the barrel 22 to remove any air bubbles in the barrel 22 as filling the syringe 10 commences.

The plunger tip 14 is mounted on a first end of the plunger rod 16, such that the plunger rod 16 extends from the center of the rear face 40 of the plunger tip 14. The plunger rod 16 is preferably made from a plastic material such as polypropylene. Movement of the plunger rod 16 along the axis of the barrel 22 causes the plunger tip 14 to slidably move within the barrel 22. As shown in FIG. 2, the plunger rod 16 is long enough so that the second end of the plunger rod 16 extends outside of the first end of the barrel 22 when the front face 38 of the plunger tip 14 is in contact with the second end of the barrel 22.

As shown in FIG. 1, the plunger rod 16 is preferably U-shaped in cross section. This design provides several advantages. First, the U-shaped plunger rod 16 makes it easy for a user to correctly position the syringe 10 within the infusion pump 36. As shown in FIG. 4, a corresponding U-shaped opening 42 in the infusion pump 36 makes it possible for a user to insert the syringe 10 in only one way—i.e., so that the U-shaped plunger rod 16 fits within the U-shaped opening 42. Second, the U-shaped plunger rod 16 permits a more compact infusion pump design because, as shown in FIG. 3, the lead screw 44 that drives the slide 46 within the infusion pump 36 can sit within the open center of the plunger rod 16 and still rotate freely. It should be appreciated by those skilled in the art that the cross-sectional shape of the plunger rod 16 could be varied without departing from the spirit and scope of the invention. For example, the cross-section of the plunger rod 16 could be hemispherical, triangular, or comprise half of a square or rectangle and still provide the above-described advantages.

As shown in FIG. 2, a groove 48 is placed on the outer surface of the plunger rod 16 adjacent to the second end of the plunger rod 16. The groove 48 provides a point at which a user can grasp the plunger rod 16, either with fingers or a device such as a C-clip, and pull the plunger rod 16 in the direction away from the connector 28 along the axis of the barrel 22 in order to fill the syringe 10. It should be understood by those skilled in the art that other structures could be placed on the plunger rod 16 to provide a grasp point for users without departing from the spirit and scope of the invention. For example, a raised rib could replace the groove 48.

Finally, a plurality of axial ribs 47 are preferably positioned along the entire length of the plunger rod 16 up to the groove 48. For example, as shown in FIG. 1, one rib 47 is preferably placed at the base of the "U" (when viewing the plunger rod 16 in cross-section) and two other ribs 47 are placed at equidistant points spaced apart from the ends of the "U." The ribs 47 are preferably integrally molded with the plunger rod 16, and provide additional strength and stability for the plunger rod 16. It should be appreciated by those skilled in the art that the number and position of the axial ribs 47 could be varied without departing from the spirit and scope of the invention.

The end cap 18, shown in FIG. 1, is attached to the first end of the barrel 22. The end cap 18 is preferably made from a plastic material such as polypropylene and can be attached to the first end of the barrel 22 by any suitable means such as, for example, with adhesives or by ultrasonic welding. The end cap 18 has an opening 50 that is shaped to complementarily receive the plunger rod 16 through which the plunger rod 16 extends. As shown in FIG. 1, a "D"-shaped opening 50 is used with the "U"-shaped plunger rod 16. The end cap 18 serves as a stop for the plunger tip 14 that prevents the plunger tip 14 from coming out of the barrel 22. Additionally, the opening 50 provides two additional features. First, the opening 50 keeps the plunger rod 16 aligned with the central axis of the syringe body. This prevents misalignment and thus leakage of medication past the tip 14 from the first end of the barrel 22. Stated another way, the opening 50 keeps the plunger rod 16 and tip 14 from going out of axial alignment with the syringe body 12. For example, as the plunger rod 16 is pushed toward the connector 28 for medication delivery, the plunger rod 16 remains parallel to the axis of the syringe body 12 without any side-to-side movement. Second, the opening 50 prevents the syringe body 12 from rotating around its central axis relative to the plunger rod 16. This is important since it prevents the syringe body 12 from rotating when an infusion set or tubing is attached by twisting on to the connector 28 and the locking mechanism 30, with adequate torque in order to obtain a good seal and avoid any medication leakage.

To assemble the syringe 10, the plunger tip 14 is attached to the plunger rod 16 and the plunger tip 14 is inserted into the syringe body 12. The end cap 18 is then attached to the syringe body 12 over the plunger rod 16. Finally, the sealing ring 20 is placed in the groove 34.

In operation, a user first attaches a hypodermic needle (not shown) to the connector 28 in the syringe body 12 and then pulls the plunger rod 16 out to the end of the syringe body 12 to draw the maximum volume of air into the syringe body 12. Then, the hypodermic needle is inserted into a medication bottle (not shown) through a rubber septum (not shown). The plunger rod 16 is then pushed towards the connector 28 as far as it will go to transfer all the air in the syringe body 12 into the medication bottle. With the syringe 10 upside down and making sure that the tip of the hypodermic needle remains below the medication fluid level, the syringe 10 can then be filled with medication by pulling back on the plunger rod 16 until the desired amount of medication is drawn into the syringe body 12 as indicated by the volume levels 37. If any air bubbles remain in the syringe 10, the plunger rod 16 is again pushed all the way towards the connector 28 to empty the medication and force any remaining air bubbles into the medication bottle. The syringe 10 is then filled with medication by pulling the plunger rod 16 to the desired volume, indicated by the volume levels 38. This process is repeated until all the air bubbles are removed and the syringe 10 is filled to the desired level.

The syringe 10 can then be inserted into the infusion pump 36. The syringe 10 is inserted with the plunger rod 16 first entering the opening 42 in the infusion pump 36. The syringe 10 is rotated until the alignment notch 58 aligns with the alignment pin 56 and the plunger rod 16 aligns with the opening 42. The syringe 10 then can be pushed into the infusion pump 36 until the flange 32 contacts the outer wall 52 of the infusion pump 36. When the syringe 10 reaches that point, the sealing ring 20 is positioned so that an interference fit is formed between the sealing ring 20 and the outer wall 52 of the infusion pump 36. A watertight seal between the inside and outside of the infusion pump 36 is thereby created. Finally, the door 54 of the infusion pump 36 can be closed and an infusion set or tubing (not shown) can be attached to the connector 28 and the locking mechanism 30 for delivering the medication contained in the syringe 10 to a desired site.

Rotation of the lead screw 44 in the infusion pump 36 causes the slide 46 to move towards the syringe body 12, which in turn drives the plunger rod 16 towards the connector 28. This forward motion of the plunger rod 16 pushes medication in the syringe body 12 through the connector 28 and into the infusion set or tubing (not shown).

It will be appreciated by those skilled in the art that changes could be made to the embodiment described above, as noted above, without departing from the broad inventive concept thereof. It is understood, therefore, that this invention is not limited to the particular embodiment disclosed, but it is intended to cover modifications within the spirit and scope of the present invention.

What is claimed is:

1. A syringe for use with an infusion pump, the infusion pump having a cavity for receiving the syringe, the cavity including a shaped opening for guiding the syringe upon insertion into the cavity, the syringe comprising:
    a syringe body comprising a tube that is open at a first end and a tapered transition to a passage at a second end and a connector extending from the passage, the connector for attachment to an infusion set or tubing; and
    a plunger slidably mounted inside the tube comprising a plunger tip having a front face that is complementarily received by the tapered second end of the tube, the plunger tip forming an interference fit with the tube, and a plunger rod having a first end attached to the plunger tip and a second end projecting outside the first end of the tube, the plunger rod having a cross-sectional shape at least partly conforming to the shape of the shaped opening in the cavity and wherein the cross-sectional shape of the plunger rod is substantially U-shaped, the plunger rod being unobstructed for purposes of longitudinal insertion of the syringe through the shaped opening in the cavity.

2. The syringe of claim 1 wherein the tube is generally circular in cross section.

3. The syringe of claim 1 wherein the second end of the tube is generally conical in shape.

4. The syringe of claim 1 wherein the transition from the tube to the second end of the tube comprises rounded corners.

5. The syringe of claim 4 wherein the transition from the second end of the tube to the passage comprises rounded corners.

6. The syringe of claim 1 wherein the connector is a Luer connector.

7. The syringe of claim 1 wherein the connector further comprises a locking mechanism.

8. The syringe of claim 7 wherein the locking mechanism is an integral Luer-lock.

9. The syringe of claim 1 further comprising a flange that extends around a periphery of the tube, the flange positioned between the second end of the tube and the connector, the flange having a diameter that is greater than the diameter of the tube, and wherein the flange and an outer surface of the second end of the tube form a groove.

10. The syringe of claim 9 wherein the flange includes a notch for being aligned with a corresponding pin in the infusion pump upon insertion of the syringe into the infusion pump.

11. The syringe of claim 9 wherein the flange is generally circular.

12. The syringe of claim 9 further comprising a sealing ring seated in the groove, wherein the flange and the sealing ring are capable of forming a watertight seal between the syringe and the infusion pump when the syringe is inserted into the cavity of the infusion pump.

13. The syringe of claim 1 further comprising a groove on the plunger rod adjacent to the second end of the plunger rod.

14. The syringe of claim 1 further comprising a plurality of axial ribs extending from the first end of the plunger rod to the second end of the plunger rod.

15. The syringe of claim 1 further comprising an end cap attached to the first end of the tube having an opening that is shaped to complementarily receive the plunger rod.

16. The syringe of claim 15 wherein the cross-sectional shape of the plunger rod is substantially U-shaped and the end cap includes an opening that is substantially U-shaped to complementarily receive the plunger rod substantially preventing the plunger from lateral movement within the tube and providing alignment with the tube.

17. The syringe of claim 15 wherein the end cap maintains the alignment of the plunger rod along the central axis of the syringe body.

18. The syringe of claim 1 wherein the transition from the tube to the second end of the tube comprises rounded corners, and the transition from the second end of the tube to the passage comprises rounded corners.

19. A syringe for use with an infusion pump, the infusion pump having a cavity with a U-shaped opening for guiding the syringe upon insertion into the infusion pump, the syringe comprising:

a syringe body comprising a tube having a tapered first end and an open second end, the first end being adapted for connection to an infusion path or tubing;

a plunger slidably mounted inside the tube, the plunger forming a fit with the tube such that no liquid passes between the tapered first end and the second end when the plunger is mounted in the tube;

a plunger rod attached to the plunger and projecting axially beyond the second end of the tube, the plunger rod having a cross-sectional shape that is substantially U-shaped and correspondingly shaped to the U-shaped opening in the cavity, the plunger rod being unobstructed for purposes of longitudinal insertion of the syringe through the U-shaped opening into the infusion pump.

\* \* \* \* \*

UNITED STATES PATENT AND TRADEMARK OFFICE
CERTIFICATE OF CORRECTION

PATENT NO. : 6,652,493 B1
DATED : November 25, 2003
INVENTOR(S) : Kusal K. Das

It is certified that error appears in the above-identified patent and that said Letters Patent is hereby corrected as shown below:

<u>Column 6,</u>
Line 60, delete "includes an" and delete "that".

Signed and Sealed this

Ninth Day of March, 2004

JON W. DUDAS
*Acting Director of the United States Patent and Trademark Office*